United States Patent [19]

Trumbore

[11] Patent Number: 4,505,149
[45] Date of Patent: Mar. 19, 1985

[54] METHOD AND APPARATUS FOR DETERMINING MOLECULAR WEIGHT

[75] Inventor: Conrad N. Trumbore, Newark, Del.

[73] Assignee: University of Delaware, Newark, Del.

[21] Appl. No.: 460,439

[22] Filed: Jan. 24, 1983

[51] Int. Cl.³ ............................................. G01N 31/08
[52] U.S. Cl. ..................................... 73/53; 73/61.1 C
[58] Field of Search .................. 73/53, 61.1 C, 55, 54

[56] References Cited

U.S. PATENT DOCUMENTS

| | | | |
|---|---|---|---|
| 3,422,667 | 1/1969 | Hrdina | 73/53 |
| 3,837,217 | 9/1974 | Schulz | 73/61.1 C |
| 4,258,564 | 3/1981 | Hulme et al. | 73/61.1 C |

OTHER PUBLICATIONS

A. Ouano, Gel Permeation Chromatography VII, Molecular Weight Detection, 1973.
"Early Phases of the Dispersion of a Sample Injected in Poiseuille Flow", by Marcel J. E. Golay and John G. Atwood, Journal of Chromatography, 186, (1979), 353–370.
"Dispersion of Peaks by Short Straight Open Tubes in Liquid Chromatography Systems", by John G. Atwood and Marcel J. E. Golay, Journal of Chromatography, 218, (1981), 97–122.

Primary Examiner—Stewart J. Levy
Assistant Examiner—Hezron Williams

[57] ABSTRACT

A method and apparatus for determining the molecular weight of an unidentified liquid component of given molecular weight by flow through an open capillary tube in the range of $N=$ about 0.1 to $N=$ about 10.0 where $N=$ number of theoretical plates in the tube length $=(2 DL/F)$, where $L=$ tube length, $F=$ flow rate and $D=$ the diffusion coefficient of the liquid component comprising passing the liquid component in plug flow within a mobile liquid phase at a preselected flow rate through an open discharge capillary tube of preselected diameter and length, obtaining a chromatogram of the eluted component over a time period of at least twice the break-through time period, measuring the vertical heights $h_1$ and $h_2$ of the chromatogram at times $t_1$ equal to 1.2 times the break-through time and $t_2$ equal to 2.0 times the break-through time, computing the ratio R of the heights $h_1$ and $h_2$, and obtaining the molecular weight of the liquid component by reference to a standard plot of the ratio R versus molecular weights for a multiplicity of different liquid component samples of known molecular weight tested under the same conditions in the same apparatus and mobile liquid phase as the sample and lying within the range of analytical interest.

6 Claims, 8 Drawing Figures

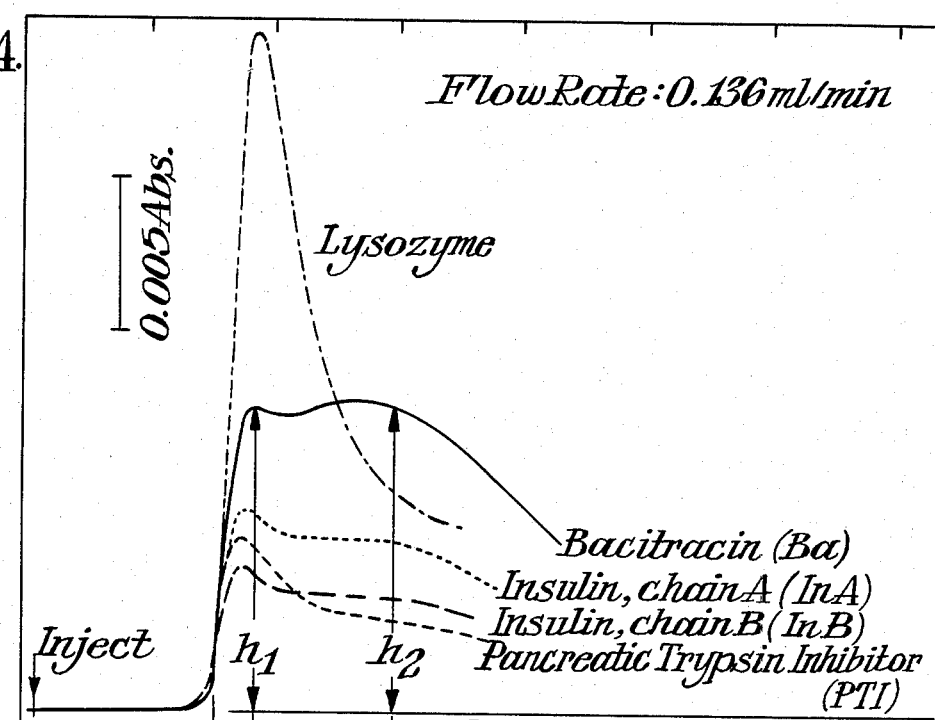
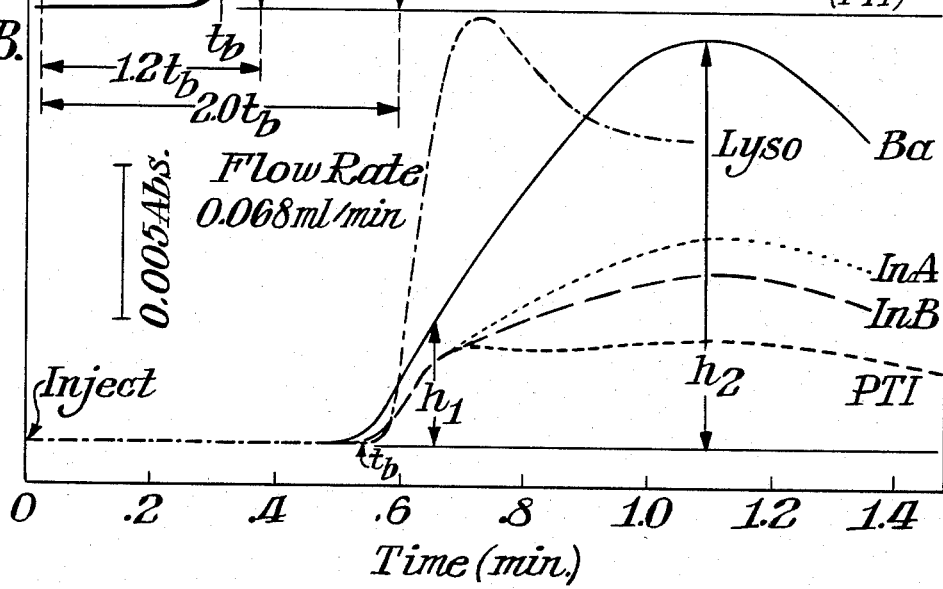
Fig. 4A.
Fig. 4B.

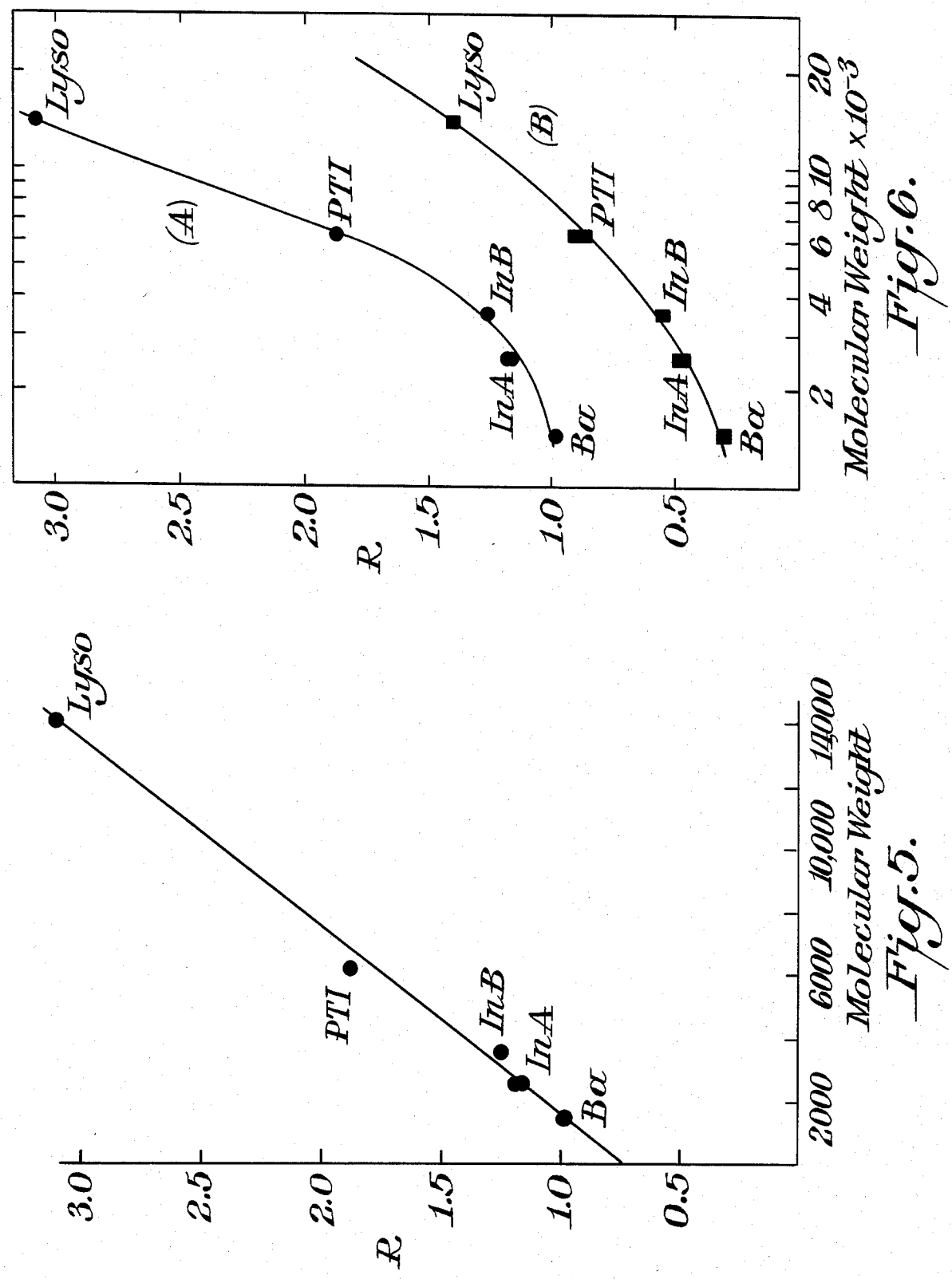

METHOD AND APPARATUS FOR DETERMINING MOLECULAR WEIGHT

BACKGROUND OF THE INVENTION

The existence of flow patterns for liquid samples in plug flow through open capillary tubes which yield unanticipated chromatographic shapes is described by mathematical model and verified by actual example by Golay and Atwood, Jl. of Chromatography 186 (1979) 353–370. These authors extended their investigation, particularly as regards relatively short tubes and curved tubes, in Jl. of Chromatography, 218 (1981) 97–122.

SUMMARY OF THE INVENTION

This invention is a method and apparatus for obtaining the molecular weight of an unidentified liquid component of given molecular weight by passing a specimen in plug flow in a mobile liquid phase preserving laminar flow through an open bore capillary tube with open discharge end, obtaining a chromatogram extending over at least twice the elution break through time, measuring the vertical heights $h_1$ and $h_2$ from base line to chromatogram trace at time intervals of 1.2 and 2.0 times the break-through time, respectively, to obtain a ratio $R=(h_1/h_2)$, and then reading the molecular weight of the liquid component by reference to a standard plot of R versus molecular weights for a multiplicity of different liquid component samples of known molecular weight tested in the same apparatus and under the same conditions, including the same mobile liquid phase, within the range of analytical interest.

The advantages of my method include rapid determination of molecular weight, small sample size required (4 $\mu$g or less), by sample nondestructive techniques in relatively rugged inexpensive equipment suitable for use in demanding plant environments.

DRAWINGS

The following drawings, constituting part of this disclosure, are schematic representations as follows:

FIG. 1 is a block diagram in side elevation of a preferred embodiment of apparatus according to this invention, FIG. 2 is a sketch of five typical chromatogram shapes which are encountered in the analytical range of $N = <0.1$ to $N>10$, where $N$ = the number of theoretical plates in the testing tube length, FIG. 3 is a representation of an actual chromatogram trace obtained in the analysis of bacitracin according to this invention, wherein the time interval for elution break-through $t_b$ together with the applicable time period values for 1.2 $t_b$ and 2.0 $t_b$ are denoted as well as the respective heights of their corresponding verticals $h_1$ and $h_2$, which are each measured to determine the ratio $h_1/h_2 = R$ according to this invention, FIG. 4 is a superposed plot of chromatograms for five specific proteins, wherein 4A is the plot for a flow rate of 0.136 ml./min. and 4B is the plot for a flow rate of 0.068 ml./min., FIG. 5 is a standard plot of R values v. molecular weight (log scale) for the component chromatograms shown in FIG. 4A, FIG. 6 is a standard plot of R values v. Molecular Weight $\times 10^{-3}$ for the components of and at the flow rates described in FIG. 4, and FIG. 7 is a standard plot of R values v. Molecular Weight over the molecular weight range of about 50 to 160,000, with extrapolation beyond.

DETAILED DESCRIPTION OF THE INVENTION

Figure 1:
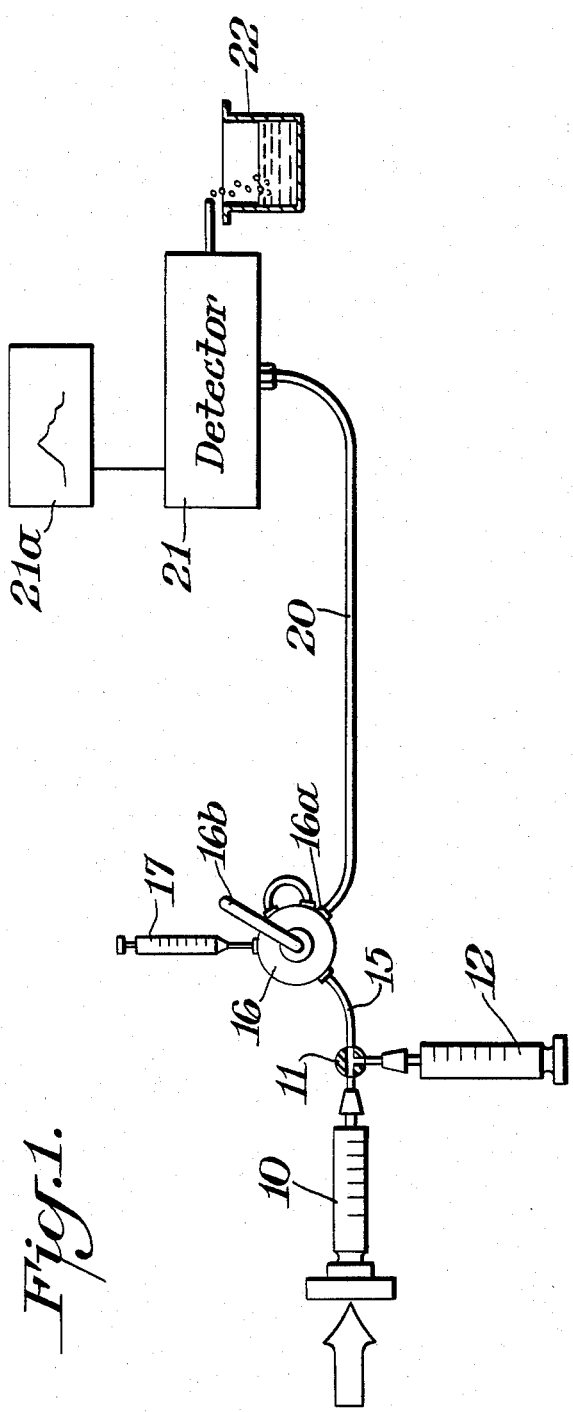

Referring to FIG. 1, the apparatus employed in this invention comprises, from left to right in serial order of liquid flow, a syringe pump 10, e.g. Sage Model 341A, for introducing the mobile phase liquid, connected to one inlet of a tee connection 11, a second inlet of which is connected to a syringe pump 12 for occasional introduction of wash liquid. The outlet of tee 11 is connected via supply tube 15 to one port of a 3-way sample injection valve 16 (e.g., a Valco Model CV-6-H Pax 3000 psig) to a second port of which sample is introduced into the injection valve sample loop by manipulation of valve handle 16b. The discharge port 16a of valve 16 is connected to the capillary flow tube 20, the open end of which discharges into standard High Performance Liquid Chromatographic (HPLC) detector 21, which feeds a signal to the recorder 21a which plots concentration signal v. time on recorder 21a. Sample effluent is collected in beaker 22.

The mobile phase liquid must be preselected to: (1) allow Brownian motion diffusion of individual sample molecules therethrough, and (2) be capable of attaining and maintaining laminar flow through the full length of capillary flow tube 20 under the flow rate necessary to achieve the desired chromatographic peak shapes. In addition, the mobile phase should not alter the molecular form of the sample, e.g., by causing aggregation or precipitation.

Typical examples of mobile phase liquids are the following:

(a) aqueous sodium phosphate buffer, pH 7.0,
(b) 0.1M sodium acetate, 0.1M $Na_2SO_4$ in water solution, pH 5,
(c) water.

The analytical sample may be as small as 0.1 $\mu$L or as large as 100 $\mu$L, depending on the inside diameter of capillary tubing 20 used. It is essential that the sample be presented to the mobile phase as a plug completely filling the capillary sample loop of injection valve 16. In addition, the plug sample should have a volume no greater than about 0.1 the total volume of capillary tube 20.

It is generally necessary that the sample be dissolved in the same liquid as the mobile phase. Sample concentration must be such that it can be detected by concentration detector 21 after diffusion within and dilution by the mobile phase in the capillary. A sufficiently high signal-to-noise ratio must exist so that precise measurements may be made of the peak heights in different chromatographic profiles. The acceptable limit of sample concentration would be that at which the sample is completely soluble and also that the detector signal is, at all times, linearly related to the sample concentration.

Connection 16a between sample injection valve 16 and capillary 20 should be by flush fit with zero dead volume. In addition, turbulence should not occur at any test flow rate at, or near, this connection.

Capillary tube 20 can be fabricated from a wide variety of materials, e.g., stainless steel, Teflon ®, glass or a number of metals, so long as the sample does not adhere to the inside tube surface at the flow rates employed. Chromatographic peak shapes should be identical in successive sample injections under identical flow rates and other experimental parameters. If they are not, then repeated shapes must be obtained with cleaning agents used between injections.

Cleaning agents which have proved effective between protein sample injections include Triton®X-100, ethanol and 2-propanol.

Capillary tubes 20 ranging from about 0.15 mm to about 1.5 mm inside diameter can be employed. Capillary tube lengths depend on the molecular weights to be determined and the flow rate employed, e.g., the greater the molecular weight the shorter the tube; however, practical constraints set the range of lengths from about 10 cm to about 200 cm.

The arrangement of apparatus should be such that tubes 20 lie generally in a linear horizontal configuration. The choice of tube length employed in a given instance is dictated by the formula for N=number of theoretical plates discussed hereinafter, and is intimately associated with the flow rates employed.

Flow rates through tube 20 should be preselected to give laminar flow throughout the apparatus from injection valve 16 to concentration detector 21. Typical values will be the minimum stable flow rate provided by the syringe pumps 10 and 17 (approximately, 20 $\mu$L/min.) to the maximum that allows sufficient diffusion time to give a double-peaked chromatogram without developing turbulent flow (e.g., about 200 $\mu$L/min. for a 0.25 mm I.D. tube).

Generally, molecular weight measurements are conducted at room temperature, i.e., 23°±1° C., but they can be conducted at higher or lower temperatures, with the following limitations:

a. the temperature should be uniform over the entire apparatus length to approximately ±0.1° C., b. laminar flow must be maintained, and c. the sample must not aggregate or precipitate within the apparatus.

Concentration detector 21 can be a standard HPLC detector of concentration versus time yielding an analog signal output to a recorder 21a which plots the concentration signal versus time. The union between the discharge end of capillary tube 20 and detector 21 should not induce turbulence, and the detector cell volume should be small (approximately 10 $\mu$L) in comparison with the volume of the liquid in the capillary (typically, 200 $\mu$L).

Figure 2:
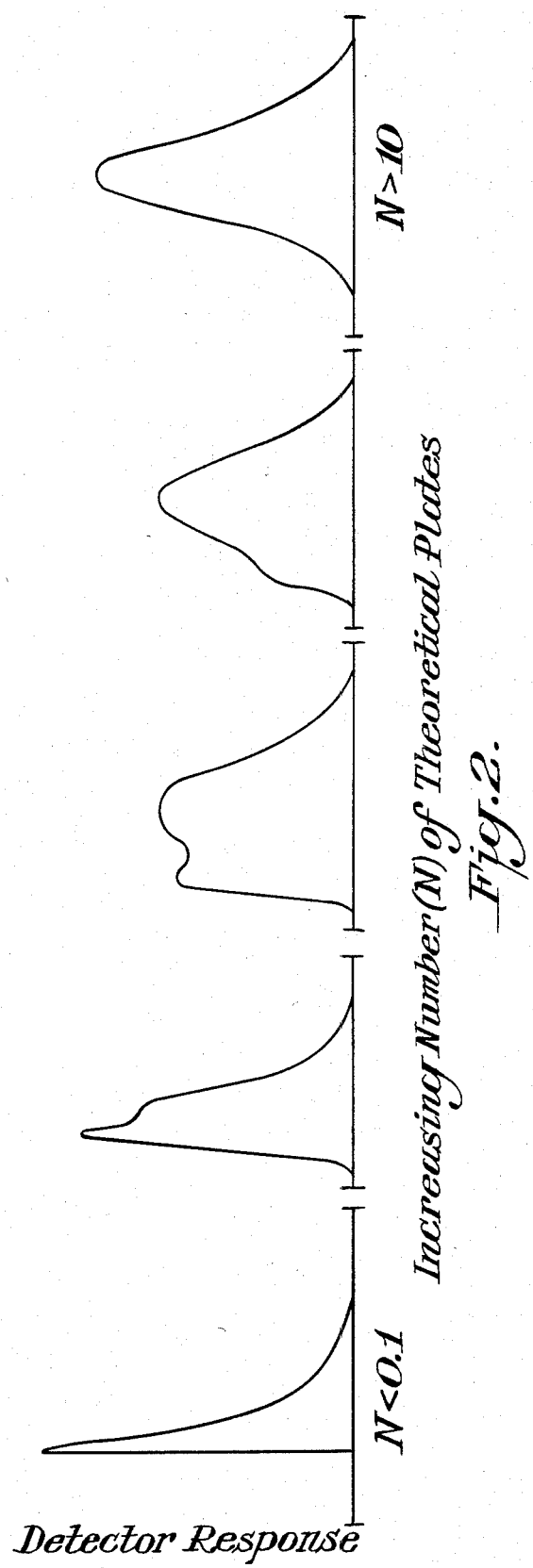

In operation, with the apparatus hereinbefore described, injection of a one-component sample in plug flow via valve 16 results in a typical family of chromatogram shapes shown schematically in FIG. 2 spaced over the range of N extending from N<0.1 for the left-hand chromatogram through N>10 for the right-hand chromatogram.

The chromatogram shapes correspond generally to those computed and observed by Atwood and Golay (Jl. Chromatography, 218 (1981) pp. 97-122) and the middle three of FIG. 2 are denoted "double-peaked" curves, which are typical of those obtained within the range of N between about 0.1 and about 10.0.

Atwood and Golay (ibid) postulated the equation $N=(24\pi DL/F)$ where N=the number of theoretical plates within a capillary 20 of given length, D=the diffusion coefficient of the liquid sample in analysis, L=the length of capillary 20 and F=the flow rate of the sample material within capillary 20.

Referring to FIGS. 2, at low N values (e.g., those below about 0.1) chromatogram shapes having a single peak with a steep leading edge and a trailing back slope are obtained, such as shown by the left-hand shape. In this N region, sample flow within an open capillary is primarily in the convection mode. As N increases in moving to the right in FIG. 2, sample flow becomes more diffusional, so that the successive chromatogram shapes become progressively more gaussian and, at the same time, they develop well-defined double peaks.

Molecular weights are determined according to this invention within the range N≈0.1-10.0 by preselecting the capillary length, the flow rate, or both, or obtain the desired chromatogram shape.

Figure 3:
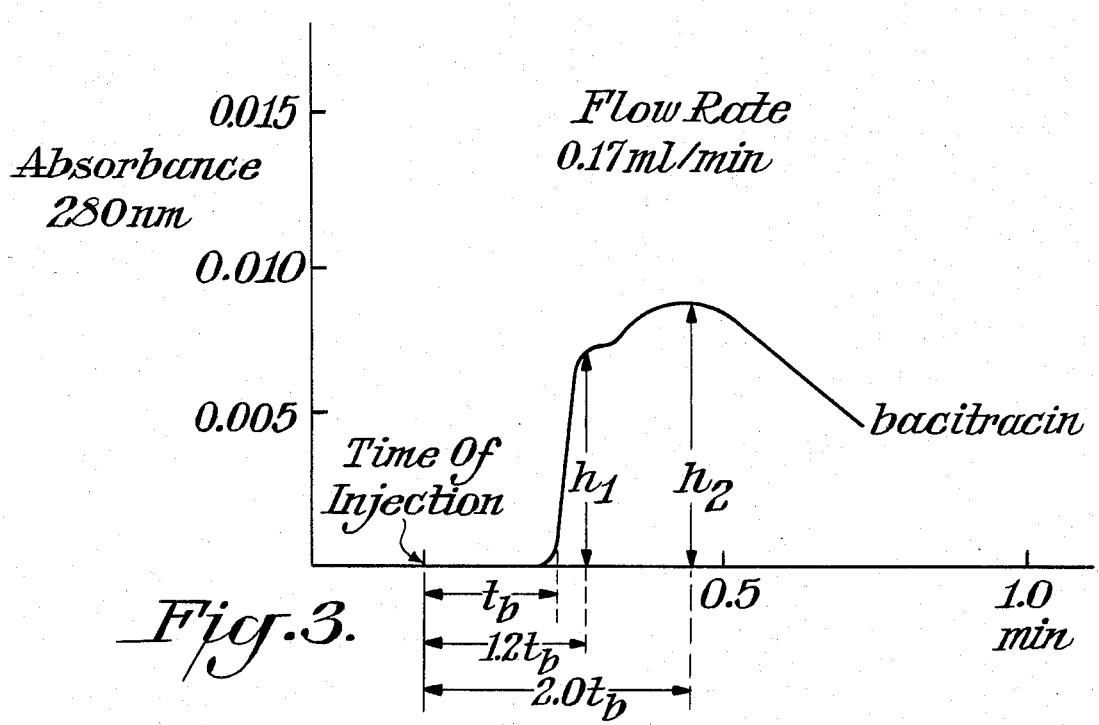

Although pronounced double-peaked chromatograms are not necessary to the operation of this invention, most analyses are conducted throughout this region and, thus, such a chromatogram is chosen for the example shown in FIG. 3. This chromatogram is an accurate profile of one obtained in the analysis of bacitracin.

Referring to FIG. 3, this invention depends upon the precise measurement of the verticals $h_1$ and $h_2$ drawn to the chromatogram profile at two exact points in time based upon the time of sample break-through, $t_b$, constituting the time span measured from the time of sample injection to the time of sample elution, as signaled by recorder 21a. The determinative points in time are 1.2 $t_b$ and 2.0 $t_b$, scaled off on the abcissa in FIG. 3, and the verticals $h_1$ and $h_2$, respectively, corresponding to these times intersect double-peaked chromatograms near the maxima of the convection peak and the diffusion peak, respectively.

I have found that the ratio, R, of $h_1$ to $h_2$ is a function of the molecular weight of liquid components in analysis according to this invention, as clearly shown in the plots of FIGS. 5, 6 and 7 as hereinafter discussed.

First, however, it is helpful to understanding to consider FIG. 4, the plots 4A and 4B of which each constitute actual example tests on five proteins having the respective molecular weights, in ascending order: Bacitracin 1450; Insulin, Chain A, 2500, Insulin, Chain B, 3500; Pancreatic Trypsin Inhibitor (PTI) 6155; and Lysozyme 14,000. The axes are Time (min.) abscissa v. Detector Response ordinate at the respective Absorbance values denoted.

The plots of FIGS. 4A and 4B are superposed one over the other, to facilitate comparison from the standpoint of elapsed time, plotted on the abscissa, the common sample introduction time point being denoted $t_i$. All sample plots extended for more than 2.0 times the sample break-through time, thus constituting complete tests.

The chromatograms of FIG. 4A were obtained at a sample flow rate of 0.136 ml./min. and those of FIG. 4B at a sample flow rate of 0.068 ml./min. Test conditiions for the two plots were otherwise identical, these being: 2 $\mu$L injections of a 2 mg./ml. solution of each individual protein into a capillary tube 20 having an inside diameter of 0.25 mm and 45 cm length, which was connected to the 17 cm cell inlet tubing of LKB 2138 Uvicord S UV monitor (LKB Instruments, Sweden) 21, not detailed, operated at 280 nm, through a Valco Instruments Company, Model CV-6-H Pax 3000 psig manual liquid chromatography sample injection valve 16 having a 1/16" zero dead volume fitting, the liquid mobile phase for which was 50 mM sodium phosphate buffer, pH 7.0.

From an examination of FIGS. 4A and 4B, it will be seen that chromatogram shapes are affected markedly by sample flow rate, lower flow rates reducing the heights of the first (convection) peaks somewhat, while increasing the heights of the second (diffusion) peaks. At the same time, the lower sample flow rates shift the traces laterally, as well as broadening them somewhat, which can be advantageous in molecular weight determinations, since this affords the technician flexibility in the choice of the portion of the analytical curve to which resort is made for molecular weight determination.

Once the analytical range of interest is settled upon, a standard curve of $R=h_1/h_2$ versus molecular weight can be constructed. If a series of liquid components of known molecular weights is selected extending over the range of interest, the corresponding R values obtained with the same apparatus operated under the same conditions and same mobile liquid phase as for the liquid component of interest can be plotted against molecular weight.

FIG. 5 is a standard plot of R versus molecular weight covering the full molecular weight range inclusive of bacitracin (MW 1450) through lysozyme (MW 14,000), the chromatograms of which are shown in FIG. 4A. This is a linear plot, permitting convenient interpolation over the full abscissa range.

Referring to FIG. 6, plotting of molecular weight values on a logarithmic absicissa scale, as here shown, gives non-linear plots, particularly in the low molecular regions of the figure. However, a decided curve shift can be achieved by appropriate preselection of the flow rates, which enables an investigator to obtain enhanced sensitivity in the determination of molecular weight as by resort to the steeper slope portion of the curve of FIG. 6A. The technique described is a direct consequence of the chromatogram shifts obtained in FIG. 4.

Figure 7:
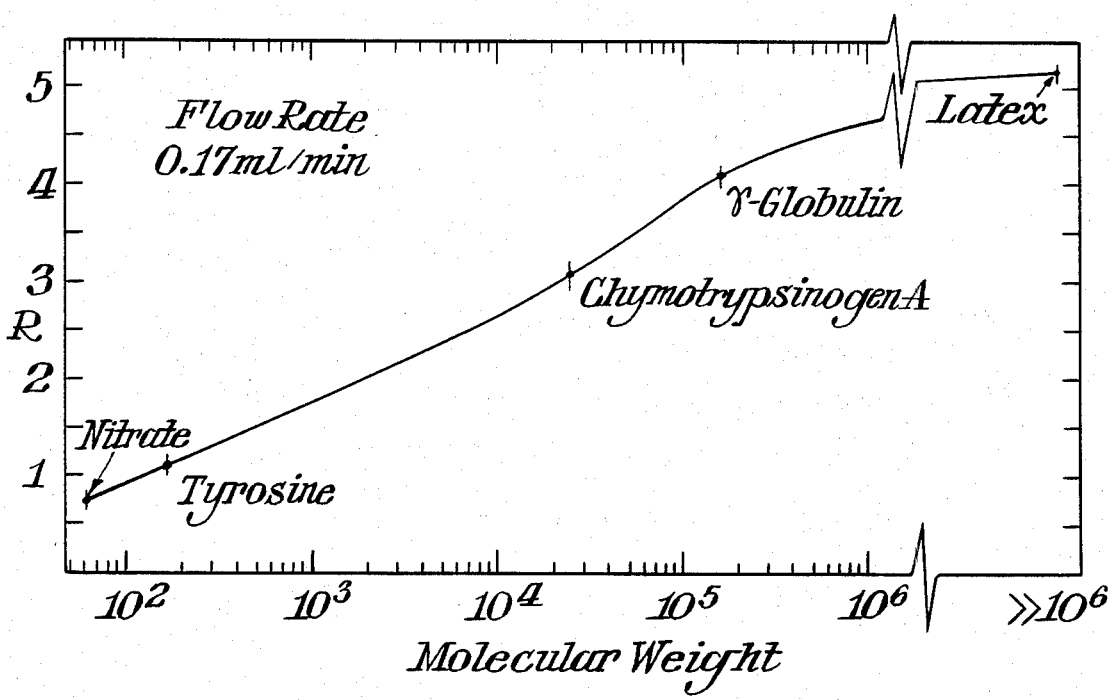

FIG. 7 is an extended plot of R v. Molecular Weight, which was produced as follows: R values were calculated from chromatograms produced by 3 μL injections into a capillary tube 20 of 0.25 mm I.D. and 45 cm length. The capillary was connected directly to a modified cell of a du Pont 837 spectrophotometer. The denoted concentrations were, respectively, 0.25M nitrate ion, 0.25 mg./ml. chymotripsinogen A, 0.5 mg./ml. gamma globulin, and $2\times10^{-4}\%$ latex. The mobile phase was water, the flow rate was 0.17 ml./min. Concentration was 0.5 mg./ml. tyrosine, mobile phase 50 mM sodium phosphate buffer, pH 7.0 Flow rate: 0.17 ml./min.

The plot of FIG. 7 is not linear; however, its gradual slope is convenient for interpolation and extends the range of molecular weight determination past gamma globulin (MW 160,000).

Very high molecular weight latex was included in FIG. 7, even though it was off the scale of the R v. Molecular Weight plot, in order to show that molecular weight determinations according to this invention are practicable in molecular weight regions orders of magnitude higher than gamma globulin. The corresponding R value at these very high molecular weights approaches asymptotic but, by appropriate preselection of flow rates, it is possible to obtain enhanced sensitivities even in these regions, as suggested by the results of FIG. 6.

Values of R in the range of about 0.2 to about 7.0 has proved advantageous for determination of molecular weight according to this invention.

What is claimed:

1. A method of determining the molecular weight of an unidentified liquid component of given molecular weight by laminar flow under isothermal conditions, within about $\pm 0.1°$ C., through a generally linear horizontal open bore capillary tube ranging from about 0.15 mm to about 1.5 mm inside diameter and about 10 cm to about 200 cm length open at the discharge end, according to $N=24DL/F$ in the range of $N=$about 0.1 to $N=$about 10.0, where $N=$the number of theoretical plates in the capillary tube length, $L=$tube length, $F=$flow rate and $D=$the diffusion coefficient of said liquid component, thereby obtaining combined convection and molecular diffusion flow comprising injecting said liquid component within a preselected mobile liquid phase into said capillary tube in a plug sample no greater than about 0.1 the volume of said capillary tube preselected to obtain a chromatographic detector trace of said liquid component linear with concentration, with a signal/noise ratio sufficiently high to determine accurately the values of chromatograms verticals $h_1$ and $h_2$ referred to the chromatogram base line, at a preselected flow rate and a preselected length of said capillary tube interrelated to achieve a value of a ratio $R=h_1/h_2$ in the range of about 0.2 to about 7.0 versus molecular weight, obtaining a chromatogram of the eluted liquid component over a time period at least twice the break-through time, measuring said vertical heights $h_1$ and $h_2$ of said chromatogram at times $t_1$ equal to 1.2 times the break-through time and $t_2$ equal to 2.0 times the break-through time, respectively, computing said ratio R of said heights $h_1$ and $h_2$ and obtaining the molecular weight of said liquid component by reference to a standard plot of said ratio R versus known molecular weights for a multiplicity of different liquid component samples evaluated under the same conditions and with the same apparatus and mobile liquid phase as said liquid component in test, and lying within the range of analytical interest.

2. A method of determining the molecular weight of an unidentified liquid component of given molecular weight by flow through a capillary tube according to claim 1 wherein said capillary tube inside diameter is preselected in the range of about 0.15 mm to about 1.5 mm.

3. A method of determining the molecular weight of an unidentified liquid component of given molecular weight by flow through a capillary tube according to claim 1 wherein said capillary tube length is preselected in the range of about 10 cm to about 200 cm.

4. A method of determining the molecular weight of an unidentified liquid component of given molecular weight by flow through a capillary tube according to claim 1 wherein said flow rates are in the range of about 20 to about 200 μL/minute.

5. A method of determining the molecular weight of an unidentified liquid component of given molecular weight by flow through a capillary tube according to claim 1 wherein said mobile liquid phase is preselected to:

(a) allow Brownian motion diffusion of said liquid component,
(b) permit the attaining and maintaining of laminar flow through said capillary tube, and
(c) not react with said liquid component in analysis.

6. Apparatus for determining the molecular weight of an unidentified liquid component of given molecular weight by laminar flow comprising, in the sequence recited, a generally linear horizontal smooth-walled open bore straight line open-ended capillary tube having an inside diameter in the range of about 0.15 mm to about 1.5 mm and a length in the range of about 10 cm to about 200 cm, proportioned according to $N=24DL/F$ in the range of $N=$ about 0.1 to $N=$ about 10.0 where $N=$ the number of theoretical plates in the capillary tube length, $F=$ flow rate and $D=$ the diffusion coefficient of said liquid component, thereby obtaining combined convection and diffusion flow, means maintaining said capillary tube under isothermal conditions within about ±0.1° C., means for injecting said unidentified liquid component together with a preselected mobile liquid phase effective to obtain combined convection and molecular diffusion flow into said capillary tube at a pressure delivering said unidentified liquid component and said mobile liquid phase at a flow rate in the range of about 20 to about 200 µL/min., chromatographic analysis means with a signal/noise ratio sufficiently high to determine accurately the values of chromatograms verticals $h_1$ and $h_2$ referred to the chromatograms' base line, at a preselected rate and a preselected length of said capillary tube interrelated to achieve a value of a ratio $R=h_1/h_2$ in the range of about 0.2 to about 7.0 versus molecular weight where said vertical heights $h_1$ and $h_2$ correspond with analysis time points $t_1$ equal to 1.2 times the break-through time, and $t_2$ equal to 2.0 times said break-through time, respectively, and obtaining the molecular weight of said liquid component by reference to a standard plot of said ratio R versus known molecular weights for a multiplicity of different liquid component samples evaluated under the same conditions and with the same apparatus and mobile liquid phase as said liquid component in test, and lying within the range of analytical interest.

* * * * *